United States Patent [19]

Kuhlmann

[11] 3,944,601

[45] Mar. 16, 1976

[54] QUALITY OF PHTHALIC ACIDS IMPROVED BY STRONG INORGANIC ACIDS

[75] Inventor: George E. Kuhlmann, Downers Grove, Ill.

[73] Assignee: Standard Oil Company, Chicago, Ill.

[22] Filed: Dec. 20, 1972

[21] Appl. No.: 316,858

[52] U.S. Cl............................................. 260/524 R
[51] Int. Cl.² ................... C07C 51/33; C07C 63/26
[58] Field of Search .............................. 260/524 R

[56] References Cited
UNITED STATES PATENTS

| | | | |
|---|---|---|---|
| 3,047,612 | 6/1962 | Pennington et al. | 260/524 R |
| 3,075,009 | 6/1963 | Keith et al. | 260/524 R |
| 3,665,030 | 5/1972 | Radzitsky et al. | 260/524 M |

FOREIGN PATENTS OR APPLICATIONS

| | | | |
|---|---|---|---|
| 841,244 | 7/1960 | United Kingdom | 260/524 R |

*Primary Examiner*—Lorraine A. Weinberger
*Assistant Examiner*—Richard D. Kelly
*Attorney, Agent, or Firm*—Fred R. Ahlers; Arthur G. Gilkes; William T. McClain

[57] ABSTRACT

Phthalic acids of improved quality are obtained direct from oxidation of xylenes with molecular oxygen in oxidation zone having less than one equivalent of strongly acidic inorganic acid per equivalent of catalyst metal present in addition to a liquid phase acetic acid solution of one or more heavy metal oxidation catalyst and bromine releasing bromide compound. Particularly useful inorganic acids are those having ionization constant $K_A$ greater than $1.0 \times 10^{-2}$, e.g. hydrobromine, nitric, sulfuric and phosphoric acids. Such quality improvement is manifested by decreased aldehydic acid and toluic acid impurity contents.

5 Claims, No Drawings

3,944,601

QUALITY OF PHTHALIC ACIDS IMPROVED BY STRONG INORGANIC ACIDS

BACKGROUND OF INVENTION

The discovery of the unique catalysis afforded by the acetic acid solution of the joint use of one or more heavy metal oxidation catalysts and a source of bromide ion for the liquid phase oxidation at a temperature from 50 to 275°C. of aliphatic-substituted aromatic compounds with molecular oxygen to aromatic polycarboxylic acid products was first disclosed in U.S. Pat. No. 2,833,816 which issued May 6, 1958. The use of said unique catalysis for such oxidation of xylenes under liquid phase conditions at 50° to 275°C. made feasible for the first time large scale commercial catalytic liquid phase production of the phthalic acids. Since 1958 many improved modes of conduct of such oxidations using the unique combination of heavy metal and bromide ion have been disclosed as advancements of that art. Some improvements were directed to yield improvement per unit of time and other improvements were directed to improved quality and yield of the phthalic acid products. In general the improved modes of conduct for said liquid phase oxidation using the unique catalysis involved use of either constant temperature or constant pressure; scheduling different rates of oxygen supply; use of sources of oxygen having oxygen contents below and above the oxygen content of air; regulation of water content of acetic acid solvent in the oxidation zone; sequentially staging of two or series connected oxidation zones operated at different temperatures, pressures, oxygen concentration or water concentration; use of different combinations of heavy metals and/or types of bromide iron source, e.g. ionic and combined bromine; and combinations thereof as applied to batchwise, semi-continuous and continuous operations. Such improved modes of operation using the unique catalysis did provide for yield increase of phthalic acid products from the yields demonstrated by the methods of U.S. Pat. No. 2,833,816. For example the yields of iso- and terephthalic acids from the corresponding isomeric xylenes were increased to 90–92 mole percent from 75–80 mole percent demonstrated by said patent with attendant improved decrease of partially oxidized xylene to such intermediates as aldehydobenzoic acid and toluic acid which contaminated said phthalic acid products.

Commercially feasible methods were devised for purifying the phthalic acid products from such improved modes of conduct of the aforementioned liquid phase oxidation using the unique catalysis. Such purifications were directed either to obtension of substantially colorless products for use in unsaturated polyesters or to obtension of iso- and terephthalic acid product of a purity of at least 99.9 weight percent for direct reaction with a diol for the preparation of polyesters of the high molecular weight required for film and fiber manufacture. However, little attention was given since 1958 to the introduction of a new component into the unique catalytic liquid phase oxidation to decrease partially oxidized xylene contaminants of phthalic acid products recovered from said oxidations.

It has been known since 1958 that oxidations of o-, m- or p-xylenes in the presence of the unique catalysis at temperatures in the range of 50° to 120°C. using oxygen gas as oxidant produced ortho-, iso- or terephthalic acid products containing relatively large amounts, 2 to 10 weight percent, of 2-, 3- or 4-formylbenzoic acid and like amounts of o-, m- or p-toluic acids. Oxidations under liquid phase conditions in the presence of the unique catalysis at temperatures above 120°C., i.e., in the range of 120° to 275°C., using oxygen gas or air as source of molecular oxygen did decrease the contaminating formylbenzoic and toluic acid contaminants in ortho-, iso- and terephthalic acid products from the corresponding xylenes to below one weight percent, e.g. 0.5–1.0 weight percent. The improved modes of conduct of the catalytic liquid phase oxidation did little to improve low temperature (i.e., 50°–100°C.) oxidations but did increase phthalic acid product yields for the higher temperature oxidations.

To make more effective, on a pounds per hour throughput basis, the various commercially available purification routes for phthalic acids it is highly desirable to obtain such phthalic acids direct from oxidation of xylenes in a higher quality by some means in addition to such improved modes of conduct of liquid phase oxidation using the unique catalysis.

SUMMARY OF INVENTION

Phthalic acids are obtained in higher quality by the oxidation of xylenes with molecular oxygen at a temperature in the range of 50° to 275°C. in an oxidation zone containing a strongly acidic inorganic acid in addition to the liquid phase acetic acid solvent solution of heavy metal oxidation catalyst and bromide ion providing the unique catalysis. The strongly acidic inorganic acid so used decreases by about 30 to about 60% the amount of formylbenzoic or toluic acid contaminant of the desired phthalic acid product and act as activators of the unique catalysis. Bromine containing inorganic acids not only cause said decrease in aldehydo acid but also can be effectively used as the source of bromine ion component of the unique catalysis. The strongly acidic acids are used in small amounts below two, preferably within the range of 0.1 to 1.9 equivalent of such acid per equivalent of metal oxidation catalyst present.

SPECIFIC EMBODIMENTS

The strongly acidic acids useful according to this invention are those having an ionization constant $K_A$ greater than $1 \times 10^{-2}$. Typical illustrative acids are hydrobromic acid, acids of phosphorus, nitric acid, sulfurous acid and sulfuric acid. When hydrobromic acid is used according to this invention the 0.1 to 1.9 equivalent per equivalents of total catalyst metal is in addition to the amount of bromine needed for the unique catalysis. The strong mono- or dibasic inorganic acid can be added to acetic acid solvent or added as a separate stream during oxidation. Since the amount of such strong inorganic acid used is relatively small and such acids are soluble in acetic acid, it is preferred to introduce the strong inorganic acid as part of the acetic acid solution of catalyst components.

The amount of acetic acid used in the catalytic liquid phase oxidation can vary from 2 to 20 weight parts per weight part of the xylene to be oxidized. For low temperature oxidation, 50° to 120°C. and atmospheric to 50 p.s.i.g. pressure the unique catalysis is provided by acetic acid solutions containing cobalt or cobalt and manganese at 13 to 112 weight percent (calculated as the metals and not salts) and 16–116 weight percent of bromide ion based on aromatic compound to be oxidized. For the higher temperature, 120° to 275°C., there can be used cobalt, manganese mixtures of cobalt and manganese or cobalt, manganese and cerium among the later defined suitable heavy metals in total metal concentrations (as distinguished from their salts) of 0.01 to 1.0 weight percent and bromide ion concentrations of 0.01 to 1.0 weight percent based on the aromatic compound. Bromide ion can be provided by elemental bromine, ionic bromides such as hydrogen bromide, sodium bromide or ammonium bromide or by co-valent bromine-containing compounds which do not ionize to bromide ion such as potassium bromate, tetrabromoethane, benzylbromide or bromobenzene or bromoacetic acid but which provide bromide ion at the temperature at which the oxidation is conducted. Mixtures of ionic and co-valent bromine compounds can be used as source of bromide ion for the oxidation. For the higher temperature oxidation heavy metals having an atomic weight between about 50 and about 200 other than cobalt, manganese and cerium or in addition thereto can be used.

The minimum pressure used in the oxidation zone is that pressure which will provide acetic acid in the liquid phase at temperatures of 50° to 275°C. The source of molecular oxygen oxidant can be any gas-containing molecular oxygen in concentrations from 10 to 100 volume percent. For the low temperature (50°–120°C.) oxidation the source of molecular oxygen can be oxygen gas or mixtures thereof with air or inert gas (e.g. nitrogen or $CO_2$) containing at least 50 volume percent oxygen. But for the higher temperature oxidation (120° to 275°C.) the source of molecular oxygen can contain not more than 50 volume percent oxygen as in air or mixtures of oxygen gas with air or inert gas to provide controllable oxidation, which is exothermic, at such higher temperatures.

The catalytic liquid phase oxidations for which this invention provides the aforementioned beneficial improvements have their most practicable application under the following temperature conditions. The low temperature (50°–120°C.) oxidation using high cobalt or cobalt and manganese to xylene and acetic acid ratios to provide most feasible production of phthalic acids especially terephthalic acid from p-xylene, per unit of time when conducted using oxygen gas, temperatures of 110° to 120°C. at pressures of 40 to 60 p.s.i.g. even though liquid phase conditions in the oxidation zone can be maintained at pressures of 0 (atmospheric pressure) to 5 p.s.i.g. Such 110° to 120°C. oxidations of p-xylene in the absence of strong acidic inorganic acid provide terephthalic acid product recovered direct (e.g. by filtration) from fluid oxidation effluent in 80–92 mole precent yields in 80–120 minute residence periods but contaminated with 5.4 to 1.3 weight percent p-formylbenzoic acid and 0.6 to 0.4 weight percent p-toluic acid. The higher temperature (120°–275°C.) oxidation using both lower acetic acid and heavy metal (Co, Mn and/or Ce) ratios to xylene provide most feasible production of phthalic acids, especially iso- or terephthalic acid from m- or p-xylene, per unit of time when conducted at temperatures in the range of 175° to 250°C. and oxidation zone pressures of 150 to 400 p.s.i.g. Such oxidations of p-xylene at 200°–210°C. and pressure of 180–210 p.s.i.g., for example in the absence of strongly acidic inorganic acid provide terephthalic acid product recovered direct from fluid oxidation effluent in 90–92 mole percent yields contaminated with but 0.5 to 0.8 weight percent p-formylbenzoic acid and 0.2 to 0.4 weight percent p-toluic acid in 40 to 60 minute residence periods.

However, by the present inventive use of strongly acidic inorganic acid having $K_A$ above $1.0 \times 10^{-2}$ in the above oxidations of p-xylene the amount of contaminant p-formylbenzoic and p-toluic acids in terephthalic acid recovered direct from fluid oxidation effluent are each decreased by from about 30 to about 60%.

The following illustrative examples are provided to enable one skilled in this art to understand and practice the present invention.

The illustrative example demonstrates the beneficial improvements afforded by the use of typically representative strong inorganic acids of $K_A$ above $1.0 \times 10^{-2}$ in the oxidation of p-xylene with air to terephthalic acid. These p-xylene oxidations are made with air at 250 p.s.i.g. oxidation zone pressure and the oxidation zone temperatures later indicated and inorganic acids later indicated. Otherwise reactants and catalyst are:

| | |
|---|---|
| 100% Acetic Acid | 1313 Grams |
| Water | 50 Grams |
| p-Xylene | 348 Grams |
| Total Co and Mn Metals | 0.12 Weight Percent on Acetic Acid |
| Bromine (Mixture of ionic and solvent) | 0.06 Weight Percent on Acetic Acid |

The oxidation reactions are conducted in an oxidation vessel having a valved air inlet at the bottom; a valved dip-leg p-xylene inlet; a heating mantle, a water cooled reflux condenser with a pressure regulating valve in its gas discharge line; a gas-vapor transfer line connecting the vapor space of said otherwise sealed vessel with said condenser; and a gas sampling top line which has a dry ice (solid $CO_2$) cooled trap and an oxygen analyzer in said gas discharge line beyond the pressure reducing valve and condenser. To such oxidation vessel there is charged the acetic acid having dissolved therein the water and sources of cobalt, manganese and bromine. The pressure regulating valve is set at operating pressure and the oxidation vessel is pressured to said pressure with nitrogen gas. The acetic acid solution is heated to oxidation temperature which causes substantially all the nitrogen gas to be discharged from the system. Thereafter the 348 grams of p-xylene is pumped and air injected simultaneously into the hot acetic acid solution at correlated rates to provide, on acetic acid free basis, a small amount (1 to 5% by volume) of oxygen in the condenser discharge gas. After all the xylene has been pumped in, air injection alone is continued for at least about 10 to 20 minutes (difference between "Run Time" and "Pump Time") until the oxygen content of the condenser discharge gas is 20 percent by volume. The reaction vessel contents are discharged with the aid of nitrogen gas pressure cooled to about 50°C. and charged to a filter to recover terephthalic acid product. The reaction vessel is rinsed to remove all solids therefrom and these solids are added to the filter cake to obtain total product. The total product is washed with warm acetic acid, dried, analyzed for p-formylbenzoic acid (4-CBA) and p-toluic acid contents and its acid number determined. The foregoing oxidation is a semi-continuous process, one of the improved methods of conduct of the aforementioned unique catalytic liquid phase oxidation methods. The conditions and results of nine such oxidations, eight using various acids including strong inorganic acids using no added acid for comparative basis are listed in TABLE I.

1.9, more preferably 0.2–1.0, equivalents per equivalent of catalyst metal can effect decrease of p-formyl-

TABLE I
EFFECT OF ADDED ACID ON p-XYLENE OXIDATION

| Example No. | Comp. | 1 | 2 | 3 | 4 | 5 | 6 | 7 | 8 |
|---|---|---|---|---|---|---|---|---|---|
| Acid Added | None | Maleic | | Oxalic | HBr | $HNO_3$ | $H_2SO_4$ | | $H_3PO_4$ |
| Acid/Metal, equivalent | 0 | 1.9 | 3.7 | 4.8 | 1.9 | 1.0 | 0.2 | 2.0 | 0.2 |
| Temperature °F., | | | | | | | | | |
| Initial | 410 | 380 | 380 | 380 | 382 | 374 | 376 | 380 | 400 |
| Maximum | 427 | 422 | 420 | 423 | 422 | 424 | 422 | 394 | 421 |
| Average | 410 | 415 | 415 | 415 | 415 | 415 | 415 | 380 | 415 |
| Run Time, Minutes | 87 | 87 | 92 | 85 | 85 | 82 | 82 | 33 | 85 |
| Pump Time, Minutes | 66 | 66 | 66 | 66 | 66 | 66 | 66 | 26 | 66 |
| Dry Product %* | 80 | 118 | 113 | 91 | 127 | 127 | 117 | 0 | 106 |
| Acid No. (Theory 675) | 660 | 672 | 670 | 669 | 673 | 673 | 674 | — | 673 |
| 4-CBA % | 1.37 | 1.13 | 1.23 | 1.35 | 0.96 | 0.60 | 0.52 | — | 0.55 |
| p-toluic Acid % | 0.30 | 0.28 | 0.34 | 0.34 | 0.15 | 0.11 | 0.10 | — | 0.11 |
| Terephthalic Acid % | 95.86 | 98.86 | 97.01 | 97.03 | 95.59 | 95.40 | 96.10 | — | 95.27 |

*Based on p-xylene charge.

During oxidation according to Example 7, all indicates of oxidation had essentially ceased (20 volume percent $O_2$ in condenser exhaust gas) after 15 minutes of p-xylene pumping, pumping was stopped at 26 minutes but air injection was continued to the 33rd minute during which time the 20 volume percent oxygen in the condenser exhaust gas was still indicated and then the run was terminated. The use of phosphoric acid at acid metal equivalent of 2.0 also adversely effected p-xylene oxidation but not to the oxidation inhibiting effect of sulfuric acid in Example 7. In fact the use of 2.0 equivalents of phosphoric acid per equivalent of catalyst metal resulted in a 128% dry product yield. Said product had an acid number of 668 and a 4-CBA content of 1.59% (more than 15% above the comparative) and p-toluic acid content of about 50% above the comparative example.

Maleic and oxalic acids are strongly acidic and, as the data in TABLE I demonstrate, do not inhibit the oxidation of p-xylene to terephthalic acid. While those strong organic acids did effect some decrease of p-formylbenzoic acid (4-carboxybenzaldehyde) from the comparative oxidation, the effects were not as significant as the effects provided by the use of strong inorganic acids.

From oxidations of p-xylene such as conducted according to Examples 4–8, it is concluded that the use of strongly acidic ($K_A$ of at least $1 \times 10^{-2}$) inorganic acids in the range of 0.1 to 1.9 equivalents per equivalent of catalyst metal is beneficial with respect to decreasing p-formylbenzoic and p-toluic acid contaminants in recovered terephthalic acid. Conduct of the semi-continuous oxidation or continuous of p-xylene at temperatures in the range of 380°–425°F. but at oxidation zone pressures of 300–400 p.s.i.g. (therefore at higher oxygen concentrations), the use of strongly acidic inorganic acids as before defined in the use range of 0.2 to 1.9, more preferably 0.2–1.0, equivalents per equivalent of catalyst metal can effect decrease of p-formyl- benzoic and p-toluic acid contaminants in recovered terephthalic acid by 30–60% of the level of such contaminants from their ranges of 0.5–1.0% obtained in the absence of such strong inorganic acids and increase terephthalic acid yield by equivalent amounts over the 90–92 mole percent yields. Likewise the use of 0.1–1.9, and more preferably 0.5–1.0, equivalents of the strong inorganic acids per equivalent of catalyst metal (equivalent of all catalyst metal present) also effects decrease of formylbenzoic acid and toluic acid contaminants in o-phthalic and isophthalic acids produced from their respective xylene isomers.

The Invention Claimed Is:

1. A method of producing a phthalic acid of improved quality from the oxidation of a xylene with molecular oxygen in an oxidation zone in the presence of a liquid phase acetic acid solution of a system of catalysis comprising a combination based on xylene of 0.1 to 112 weight percent heavy metal oxidation catalyst and from 0.01 to 116 weight percent bromine in said zone, which method consists essentially having in said liquid phase acetic acid solution the inorganic acid hydrobromic acid, sulfuric acid or phosphoric acid in an amount of from 0.1 to 1.9 equivalents thereof per equivalent of catalyst metal in addition to acidic bromine in said catalysis combination.

2. The method of claim 1 wherein the xylene is p-xylene and the equivalents of inorganic acid to equivalent of catalyst metal is in the range of 0.2 to 1.0.

3. The method of claim 2 wherein the inorganic acid is hydrobromic acid.

4. The method of claim 2 wherein the inorganic acid is sulfuric acid.

5. The method of claim 2 wherein the inorganic acid is phosphoric acid.

* * * * *